United States Patent
Rejman et al.

(10) Patent No.: US 11,135,237 B2
(45) Date of Patent: Oct. 5, 2021

(54) LIPOPHOSPHONOXINS OF SECOND GENERATION, AND THEIR USE

(71) Applicants: USTAV ORGANICKE CHEMIE A BIOCHEMIE AV CR, V.V.I., Prague (CZ); MIKROBIOLOGICKY USTAV AV CR, V.V.I., Prague (CZ); TRIOS, SPOL. S R.O., Prague (CZ)

(72) Inventors: Dominik Rejman, Prague (CZ); Radek Pohl, Uholicky (CZ); Eva Zbornikova, Libcice nad Vltavou (CZ); Libor Krasny, Roztoky u Prahy (CZ); Tomas Latal, Hlusovice (CZ); Milan Kolar, Olomouc (CZ)

(73) Assignees: USTAV ORGANICKE CHEMIE A BIOCHEMIE AV CR, V.V.I., Prague (CZ); TRIOS, SPOL. S R.O., Prague (CZ)

( * ) Notice: Subject to any disclaimer, the term of this patent is extended or adjusted under 35 U.S.C. 154(b) by 520 days.

(21) Appl. No.: 16/096,160

(22) PCT Filed: Apr. 19, 2017

(86) PCT No.: PCT/CZ2017/050017
§ 371 (c)(1),
(2) Date: Oct. 24, 2018

(87) PCT Pub. No.: WO2017/186200
PCT Pub. Date: Nov. 2, 2017

(65) Prior Publication Data
US 2021/0220383 A1    Jul. 22, 2021

(30) Foreign Application Priority Data

Apr. 28, 2016 (CZ) ................ CZ2016-243

(51) Int. Cl.
| | |
|---|---|
| *C07H 19/10* | (2006.01) |
| *A61P 31/04* | (2006.01) |
| *A01N 57/24* | (2006.01) |
| *A61K 31/7072* | (2006.01) |

(52) U.S. Cl.
CPC .......... *A61K 31/7072* (2013.01); *A01N 57/24* (2013.01); *A61P 31/04* (2018.01); *C07H 19/10* (2013.01)

(58) Field of Classification Search
None
See application file for complete search history.

(56) References Cited

FOREIGN PATENT DOCUMENTS

| | | | |
|---|---|---|---|
| CZ | 20110312 A3 | 12/2012 | |
| EP | 2527351 A1 | 5/2012 | |
| EP | 2527351 A1 * | 11/2012 | ............ A61P 31/04 |

OTHER PUBLICATIONS

Rejman, Dominik et al., "Lipophosphonoxins: New Modular Molecular Structures with Significant Antibacterial Properties", Journal of Medicinal Chemistry, vol. 54, No. 22, Nov. 24, 2011, pp. 7884-7898.
Dae-Hwan Suk, et al., "Phosphonoxins: Rational design and discovery of a patent nucleotide anti-Giardia agent", Bioorganic & Medicinal Chemistry Letters, Pergamon, Amsterdam, NL, vol. 17, No. 10, Apr. 27, 2007, pp. 2811-2816.
International Search Report and Written Opinion for corresponding PCT application PCT/CZ2017/050017, dated Jun. 12, 2017.

* cited by examiner

*Primary Examiner* — Traviss C McIntosh, III
(74) *Attorney, Agent, or Firm* — Notaro, Michalos & Zaccaria P.C.

(57) ABSTRACT

Lipophosphonoxins of general Formula I are described, in which $R_1$ is C8-C22, preferably C10-C18 and more preferably C12-C16 alkyl, or hexadecyloxypropyl, tetradecyloxypropyl, tetradecyloxyethyl or hexadecyloxyethyl, $R_2$ is uracil, thymine, or cytosine, and $R_3$ is selected from a group which contains compounds of general formulas II and III.

8 Claims, No Drawings

LIPOPHOSPHONOXINS OF SECOND GENERATION, AND THEIR USE

FIELD OF ART

The invention relates to new substances with antibacterial effects and their use in vitro and in vivo.

BACKGROUND ART

Currently, an increasing number of bacteria are becoming resistant to conventional medicines and new drugs are therefore needed for treatment of diseases caused by these resistant bacteria (Davies D., Davies J., Microbiol. Mol. Biol. Rev. 2010, 74(3), 417; Kesselheim A. S., Outterson K., Health Aff. 2010, 29, 1689).

Recently, lipophosphonoxins of first generation were reported, exhibiting activity against gram-positive bacteria (J. Med. Chem. 2011, 54(22), 7884-7898, CZ PV 2011-312, EP2527351). Furthermore, the mechanism of their effect was described, consisting of selective disruption of the bacterial membrane (PLoS One 2015, 10(12), e0145918).

Lipophosphonoxins (LPPO) are bactericidal substances with fast kinetics and they are not genotoxic. Maximum tolerated dose (MTD) in mice after oral administration is very high (>2000 mg/kg) and the bacteria are not able to develop resistance. Lipophosphonoxins are chemically stable over a broad pH range and do not pass through a monolayer of CACO-2 cells, which means that very likely, they will not be absorbed after oral administration. LPPO belong to the growing family of antibacterial peptidomimetics, such as cationic steroidal antibiotics (Ferns Microbiol Lett. 2002, 217(1):1-7; Bba-Biomembranes 2007, 1768(10), 2500-2509; J. Med. Chem. 2002 45(3), 663-669), lipophilic derivatives of norspermidine (J. Med. Chem. 2014, 57(22), 9409-9423), arylamide foldamers (Antimicrob Agents Ch. 2011, 55(11), 5043-5053; Angew. Chem. Int. Edit. 2004, 43(9), 1158-1162) or a promising synthetic bactericidal antimicrobial peptide LTX-109 (Angew Chem Int Edit 43:1158-62. Antimicrob Agents Ch 55:5043-53) which degrades the membranes of harmful microorganisms. These compounds are structurally heterogeneous; however, they are all amphiphilic molecules containing a lipophilic portion and a hydrophilic portion, usually carrying a positive charge. Lipophosphonoxins also share this structural motif; however their main advantage lies in their modular structure, allowing systematic tuning of their biological properties.

DISCLOSURE OF THE INVENTION

This invention discloses novel compounds of Formula I, which exhibit strong antibacterial activity against gram-positive and gram-negative bacteria. In addition to their easy preparation, the advantage of these compounds is their modular structure which allows further tuning of their biological properties.

The invention involves lipophosphonoxins of second generation of general formula I,

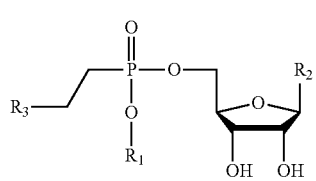
(I)

wherein:
$R_1$ is selected from C8-C22 alkyl (preferably C10-C18 alkyl and more preferably C12-C16 alkyl), hexadecyloxypropyl, tetradecyloxypropyl, tetradecyloxyetyl, hexadecyloxyetyl;
$R_2$ is selected from uracil, thymine, cytosine; and
$R_3$ is selected from the group consisting of compounds of general formulas II to V:

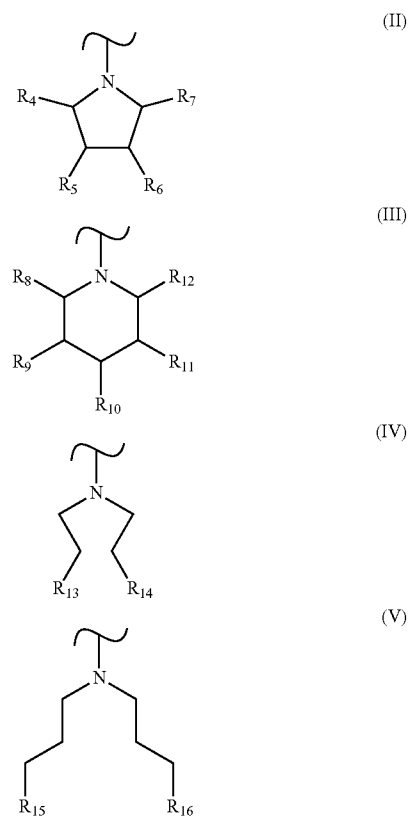

wherein $R_4$ is H, $CH_2NH_2$ or $CH_2OH$,
$R_5$ is H, $NH_2$ or OH,
$R_6$ is H, $NH_2$ or OH,
$R_7$ is H, $CH_2NH_2$ or $CH_2OH$,
whereas at least one of the groups $R_5$ and $R_6$ must be $NH_2$ or at least one of the groups $R_4$ and $R_7$ must be $CH_2NH_2$;
$R_8$ is H, $CH_2NH_2$ or $CH_2OH$,
$R_9$ is H, $NH_2$ or OH,
$R_{10}$ is H, $NH_2$ or OH,
$R_{11}$ is H, $NH_2$ or OH,
$R_{12}$ is H, $CH_2NH_2$ or $CH_2OH$,
whereas at least one of the groups $R_9$, $R_{10}$ and $R_{11}$ must be $NH_2$ or at least one of the groups $R_8$ and $R_{12}$ must be $CH_2NH_2$;
$R_{13}$ is $NH_2$ or NH—CH($NH_2$)NH,
$R_{14}$ is $NH_2$ or NH—CH($NH_2$)NH,
$R_{15}$ is $NH_2$ or NH—CH($NH_2$)NH,
$R_{16}$ is $NH_2$ or NH—CH($NH_2$)NH;
and their pharmaceutically acceptable salts and/or hydrates.

The pharmaceutically acceptable salts include salts with inorganic or organic anions and particularly, but not exclusively, pharmaceutically acceptable salts suitable for physiological administration.

Pharmaceutically acceptable salts may be salts derived from inorganic or organic acids. A person skilled in the art will be able to determine which are pharmaceutically acceptable salts; particularly they are salts having one or more desirable physical properties, such as enhanced pharmaceutical stability at different temperatures and humidities, the required solubility in water or oil, or they are non-toxic.

Suitable pharmaceutically acceptable salts of substances according to the invention preferably comprise anions derived from inorganic acids such as hydrochloric, hydrobromic, hydrofluoric, boric, fluoboric, phosphoric, metaphosphoric, nitric, carbonic, sulphurous and sulfuric acids, and organic acids such as acetic acid, benzenesulfonic, benzoic, citric, ethanesulfonic, fumaric, gluconic, glycolic, isethionic, lactic, lactobionic, maleic, malonic, methanesulfonic, trifluoromethanesulfonic, succinic, toluenesulfonic, tartaric, and trifluoroacetic acids. Suitable organic acids generally include, for example, the following classes of organic acids: aliphatic, cycloaliphatic, aromatic, araliphatic, heterocyclic, carboxylic and sulfonic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, pamoate, methanesulfonate, ethanesulfonate, benzenesulfonate, pantothenate, toluenesulfonate, 2-hydroxyethanesulfonate, sulfanilate, cyclohexylaminosulfonate, 13-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

Compounds of formula I contain several chiral centers (particularly on the phosphorus atom and in the $R_5$ group). The existence of a chiral center allows the compound to exist as one of two possible optical isomers ((R)- or (S)-enantiomer) or as a mixture, typically a racemic mixture, of both. All of the resulting diastereomers and mixtures of diastereomers are also included within the scope of lipophosphonoxins of the second generation general of formula I as described by the invention.

The invention further includes lipophosphonoxins of general formula I, or pharmaceutically acceptable salts and/or hydrates and/or mixtures of such compounds for use as medicaments.

The invention further includes lipophosphonoxins of general formula I, or pharmaceutically acceptable salts and/or hydrates and/or mixtures of such compounds for use as antibacterials.

The invention further includes an antibacterial drug, containing lipophosphonoxins of general formula I or their diastereomers, or pharmaceutically acceptable salts and/or hydrates and/or mixtures of such compounds as the active ingredient.

The present invention further includes a method of treatment of disorders caused by bacteria, comprising the step of administering at least one lipophosphonoxin of general formula I or pharmaceutically acceptable salt and/or hydrate thereof to a subject in need of such treatment.

Finally, the invention includes the use of lipophosphonoxins of general formula I or their diastereomers, or pharmaceutically acceptable salts and/or hydrates and/or mixtures of such compounds as active ingredients of disinfectants for other than therapeutic purposes, and/or use as a component of selective culivation media for in vitro cultures.

A medicament is any substance or combination of substances intended for treating or preventing disease in humans or animals and any substance or combination of substances which may be administered to humans or animals with a view to making a medical diagnosis or to restoring, improving or modifying physiological functions in humans or animals.

The substances of the invention exhibit antibacterial activities in particular against strains of *Escherichia coli, Pseudomonas aeruginosa, Enterococcus faecalis, Bacterium subtilis*, and *Streptococcus agalactiae, Staphylococcus aureus, Staphylococcus haemolyticus, Enterococcus faecium, Staphylococcus epidermidis, Salmonella enteritidis* and even against strains resistant to existing antibiotics.

Compared with the first generation LPPO (*J. Med. Chem.* 2011, 54(22), 7884-7898, CZ PV 2011-312, EP2527351), the LPPO of second generation, which are the object of the present invention, exhibit a much broader spectrum of antibacterial activity. The greatest benefit over the prior art is the fact that they are mainly effective against clinically important gram-negative bacterial strains such as *Escherichia coli, Pseudomonas aeruginosa* or *Salmonella enteritidis*. Surprisingly, they are also effective against harmful multiresistant bacterial strains occurring in the hospital environment, which were not sensitive against the first generation LPPO.

The compounds of this invention exhibit little or no effects on viability of normal human erythroid cells cultured in vitro in the range of antibacterially active concentrations of the compounds. The same applies to their induced cytotoxicity.

Modularity of the structure and easy synthesis by connecting the individual modules allows large structural variations of the compounds of this invention, which can lead to modulation of their biological activity.

EXAMPLES

List of Abbreviations

DCM dichloromethane

TPSCl triisopropylbenzenesulfonylchloride

IR infrared spectrum

HR-ESI high-resolution electrospray ionisation mass spectrum

HR-EI high-resolution electroimpact ionisation mass spectrum n-BuOH n-butylalcohol DMTr dimethoxytrityl THF tetrahydrofuran $EC_{50}$ median active (effective) concentration (causing 50% of maximum effect)

$IC_{50}$ inhibitory concentration (causing 50% of the maximum inhibitory effect)

rt room temperature

MIC minimum inhibitory concentration

MBC minimal bactericidal concentration

Example 1

Hexadecyl-uridine-5'-yl-2-N-bis (3-aminopropyl)-2-aminoethyl phosphonate

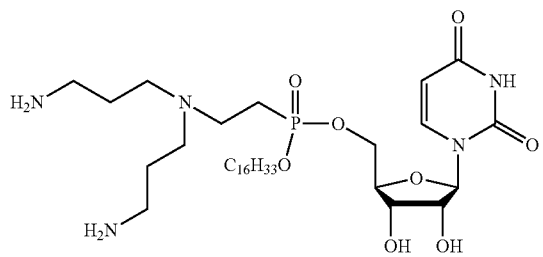

A mixture of bis boc-N-1-(3-aminopropyl)propane-1,3-diamine (0.53 g, 1.5 mmol) (prepared according to *J. Med. Chem.* 2014, 57 (22), 9409-9423) and hexadecyl-2',3'-isopropylidenuridin-5'-yl-vinylphosphonate (0.6 g, 1 mmol) (prepared according to *J. Med. Chem.* 2011, 54(22), 7884-7898) in n-BuOH (10 ml) was stirred overnight at 105° C. The reaction mixture was concentrated in vacuum and the isopropylidene-protected intermediate was purified by chromatography on silica gel using a linear gradient of ethanol in chloroform (0-10%). The resulting solid was dissolved in 0.5 mol·l$^{-1}$ HCl in methanol (40 ml) and the mixture was stirred for 12 hours at room temperature. The reaction mixture was concentrated to about half volume on rotary evaporator and added to cold ethyl acetate (20 ml). The solid obtained was filtered and dried. This resulted in the desired product as an amorphous solid in 74% yield (0.56 g, 0.74 mmol).

$^1$H NMR (500.0 MHz, CD$_3$OD): 0.90 (m, 6H, CH$_3$(CH$_2$)$_{14}$CH$_2$O); 1.24-1.43 (m, 52H, CH$_3$(CH$_2$)$_{13}$CH$_2$CH$_2$O); 1.71 (m, 4H, CH$_3$(CH$_2$)$_{13}$CH$_2$CH$_2$O); 2.15-2.25 (bm, 8H, NCH$_2$CH$_2$CH$_2$NH$_2$); 2.52-2.67 (m, 4H, PCH$_2$CH$_2$N); 3.10 (t, 8H, J$_{vic}$=7.5, NCH$_2$CH$_2$CH$_2$NH$_2$); 3.35-3.42 (bm, 8H, NCH$_2$CH$_2$CH$_2$NH$_2$); 3.44-3.52 (bm, 4H, PCH$_2$CH$_2$N); 4.10-4.21 (m, 8H, H-3',4', CH$_3$(CH$_2$)$_{14}$CH$_2$O); 4.27 (dd, 1H, J$_{2',3'}$=5.4, J$_{2',1'}$=4.2, H-2'); 4.28 (dd, 1H, J$_{2',3'}$=5.3, J$_{2',1'}$=3.9, H-2'); 4.34 (ddd, 1H, J$_{gem}$=11.6, J$_{H,P}$=7.5, J$_{5'b,4'}$=5.4, H-5'b); 4.39 (dd, 2$_{H,P}$=7.6, J$_{5',4'}$=4.3, H-5'); 4.43 (ddd, 1H, J$_{gem}$=11.6, J$_{H,P}$=7.3, J$_{5'a,4'}$=2.9, H-5'a); 5.77 (d, 2H, J$_{5,6}$=8.0, H-5); 5.84 (d, 1H, J$_{1',2'}$=4.2, H-1'); 5.85 (d, 1H, =3.9, H-1'); 7.74 (d, 1H, J$_{6,5}$=8.0, H-6); 7.75 (d, 1H, J$_{6,5}$=8.0, H-6).

$^{13}$C NMR (125.7 MHz, CD$_3$OD): 14.45 (CH$_3$(CH$_2$)$_{14}$CH$_2$O); 21.33 (d, J$_{C,P}$=140.8, PCH$_2$CH$_2$N); 21.37 (d, J$_{C,P}$=141.1, PCH$_2$CH$_2$N); 23.28 (NCH$_2$CH$_2$CH$_2$NH$_2$); 23.73, 26.57, 30.32, 30.47, 30.68, 30.75, 30.76, 30.80 (CH$_3$(CH$_2$)$_{13}$CH$_2$CH$_2$O); 31.56 (d, J$_{C,P}$=5.9, CH$_3$(CH$_2$)$_{13}$CH$_2$CH$_2$O); 31.55, 31.56 (d, J$_{C,P}$=5.9, CH$_3$(CH$_2$)$_{13}$CH$_2$CH$_2$O); 33.07 (CH$_3$(CH$_2$)$_{13}$CH$_2$CH$_2$O); 37.87 (NCH$_2$CH$_2$CH$_2$NH$_2$); 48.58 (NCH$_2$CH$_2$P); 51.09 (NCH$_2$CH$_2$CH$_2$NH$_2$); 67.37 (d, J$_{C,P}$=6.1, CH$_2$-5'); 68.37 (d, J$_{C,P}$=6.8, CH$_3$(CH$_2$)$_{14}$CH$_2$O); 68.56 (d, J$_{C,P}$=6.8, CH$_3$(CH$_2$)$_{14}$CH$_2$O); 70.81, 70.90 (CH-3'); 74.61, 74.65 (CH-2'); 83.37 (d, J$_{C,P}$=6.0, CH-4'); 83.39 (d, J$_{C,P}$=6.2, CH-4'); 92.14, 92.26 (CH-1'); 103.17, 103.21 (CH-5); 143.00, 143.04 (CH-6); 152.22, 152.28 (C-2); 165.96, 165.97 (C-4).

$^{31}$P{$^1$H} NMR (202.3 MHz, CD$_3$OD): 27.67; 28.13.

IR v$_{max}$(KBr) 3426 (s, vbr), 3047 (m, vbr), 2640 (m, vbr, sh), 2090 (w, vbr, sh), 1700 (vs, sh), 1681 (vs), 1467 (m), 1429 (w), 1390 (w), 1261 (w, br), 1206 (s), 1080 (w, sh), 1060 (m), 1021 (m, br), 1002 (m), 764 (vw, sh).

HR-ESI C$_{33}$H$_{65}$O$_8$N$_5$P (M+H)$^+$ calculated 690.45653, found 690.45656.

Example 2

Pentadecyl-uridine-5'-yl-2-N-bis(3-aminopropyl)-2-aminoethyl phosphonate

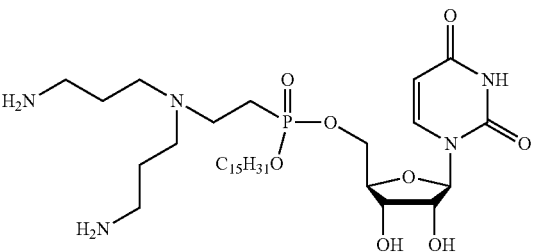

The compound in Example 2 was prepared by the same procedure as the one in Example 1 from bis boc-N-1-(3-aminopropyl)propane-1,3-diamine (0.53 g, 1.5 mmol) and pentadecyl-2',3'-isopropylidenuridine-5'-yl-vinylphosphonate (prepared according to J. Med. Chem. 2011, 54(22), 7884-7898) (0.63 g, 1 mmol) in 75% yield (0.56 g, 0.75 mmol).

$^1$H NMR (500.0 MHz, CD$_3$OD): 0.90 (m, 6H, CH$_3$(CH$_2$)$_{13}$CH$_2$O-A,B); 1.24-1.43 (m, 48H, CH$_3$(CH$_2$)$_{12}$CH$_2$CH$_2$O-A,B); 1.71 (m, 4H, CH$_3$(CH$_2$)$_{12}$CH$_2$CH$_2$O-A,B); 2.15-2.23 (bm, 8H, NCH$_2$CH$_2$CH$_2$NH$_2$-A,B); 2.52-2.62 (m, 4H, PCH$_2$CH$_2$N-A,B); 3.09 (t, 8H, J$_{vic}$=7.5, NCH$_2$CH$_2$CH$_2$NH$_2$); 3.32-3.42 (bm, 8H, NCH$_2$CH$_2$CH$_2$NH$_2$); 3.43-3.51 (bm, 4H, PCH$_2$CH$_2$N); 4.11-4.20 (m, 8H, H-3',4'-A,B, CH$_3$(CH$_2$)$_{13}$CH$_2$O-A,B); 4.26 (dd, 1H, =5.3, J$_{2',1'}$=4.1, H-2'-A); 4.28 (dd, 1H, J$_{2',3'}$=5,1, J$_{2',1'}$=3.9, H-2'-B); 4.30-4.45 (m, 4H, H-5'-A,B); 5.764 (d, 1H, J$_{5,6}$=8.0, H-5-A); 5.766 (d, 1H, J$_{5,6}$=8.0, H-5-B); 5.83 (d, 1H, J$_{1',2'}$=4.1, H-1'-A); 5.84 (d, 1H, J$_{1',2'}$=3.9, H-1'-B); 7.73 (d, 1H, J$_{6,5}$=8.0, H-6-B); 7.74 (d, 1H, J$_{6,5}$=8.0, H-6-A). $^{13}$C NMR (125.7 MHz, CD$_3$OD): 14.45 (CH$_3$(CH$_2$)$_{13}$CH$_2$O-A,B); 21.30 (d, J$_{C,P}$=140.7, PCH$_2$CH$_2$N-A); 21.35 (d, J$_{C,P}$=140.9, PCH$_2$CH$_2$N—B); 23.34 (NCH$_2$CH$_2$CH$_2$NH$_2$-A,B); 23.74, 26.58, 30.33, 30.48, 30.69, 30.75, 30.77, 30.79; 30.81 (CH$_3$(CH$_2$)$_{12}$CH$_2$CH$_2$O-A,B); 31.56 (d, J$_{C,P}$=5.9, CH$_3$(CH$_2$)$_{12}$CH$_2$CH$_2$O-A); 31.57 (d, J$_{C,P}$=5.9, CH$_3$(CH$_2$)$_{12}$CH$_2$CH$_2$O—B); 33.08 (CH$_3$(CH$_2$)$_{12}$CH$_2$CH$_2$O-A,B); 37.87 (NCH$_2$CH$_2$CH$_2$NH$_2$-A,B); 48.51 (NCH$_2$CH$_2$P-A,B); 51.12 (NCH$_2$CH$_2$CH$_2$NH$_2$-A,B); 67.41 (d, J$_{C,P}$=6.3, CH$_2$-5'-A); 67.44 (d, J$_{C,P}$=6.1, CH$_2$-5'-B); 68.36 (d, J$_{C,P}$=6.8, CH$_3$(CH$_2$)$_{13}$CH$_2$O—B); 68.56 (d, J$_{C,P}$=6.8, CH$_3$(CH$_2$)$_{13}$CH$_2$O-A); 70.84 (CH-3'-B); 70.91 (CH-3'-A); 74.59 (CH-2'-A); 74.63 (CH-2'-B); 83.35 (d, J$_{C,P}$=6.1, CH-4'-A,B); 92.31 (CH-1'-A); 92.40 (CH-1'-B); 103.13 (CH-5-A); 103.18 (CH-5-B); 143.03 (CH-6-A); 143.07 (CH-6-B); 152.20 (C-2-A); 152.27 (C-2-B); 165.98 (C-4-A); 165.99 (C-4-B).

$^{31}$P{$^1$H} NMR (202.3 MHz, CD$_3$OD): 27.65 (A); 28.10 (B).

IR v$_{max}$(KBr) 3050 (s, vbr, sh), 3411 (s, br), 2645 (m, br), 2924 (vs), 2854 (vs), 2563 (m, br), 2035 (w, br), 1975 (w, br, sh), 1690 (vs, br), 1624 (m), 1520 (m, br, sh), 1466 (s), 1408 (m), 1386 (m), 1266 (s), 1233 (s, br, sh), 1075 (s, sh), 1055 (s), 1035 (s, br, sh), 997 (s), 822 (m), 764 (w), 721 (w).

HR-ESI $C_{32}H_{63}O_8N_5P$ (M+H)$^+$ calculated 676.44088, found 676.44092.

Example 3

Tetradecyl-uridine-5'-yl-2-N-bis (3-aminopropyl)-2-aminoethyl phosphonate

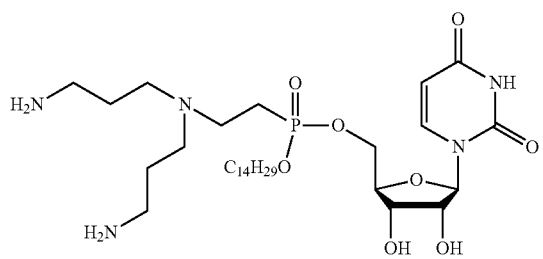

The compound in Example 3 was prepared by the same procedure as the one in Example 1 from boc-N-1-(3-aminopropyl)propane-1,3-diamine (0.62 g, 1.86 mmol) and tetradecyl-2',3'-isopropylidenuridine-5'-yl-vinylphosphonate (prepared according to J. Med. Chem. 2011, 54(22), 7884-7898) (0.76 g, 1.33 mmol) in 65% yield (0.64 g, 0.87 mmol).

$^1$H NMR (500.0 MHz, CD$_3$OD): 0.90 (m, 6H, CH$_3$(CH$_2$)$_{12}$CH$_2$O-A,B); 1.24-1.43 (m, 44H, CH$_3$(CH$_2$)$_{11}$CH$_2$CH$_2$O-A,B); 1.71 (m, 4H, CH$_3$(CH$_2$)$_{12}$CH$_2$CH$_2$O-A, B); 2.16-2.26 (bm, 8H, NCH$_2$CH$_2$CH$_2$NH$_2$-A,B); 2.54-2.65 (m, 4H, PCH$_2$CH$_2$N-A,B); 3.10 (t, 8H, J $J_{vic}$=7.5, NCH$_2$CH$_2$CH$_2$NH$_2$); 3.35-3.42 (bm, 8H, NCH$_2$CH$_2$CH$_2$NH$_2$); 3.44-3.52 (bm, 4H, PCH$_2$CH$_2$N); 4.08-4.22 (m, 8H, H-3',4'-A,B, CH$_3$(CH$_2$)$_{12}$CH$_2$O-A,B); 4.27 (dd, 1H, $J_{2',3'}$=5.4, $J_{2',1'}$=4.2, H-2'-B); 4.28 (dd, 1H, $J_{2',3'}$=5.3, $J_{2',1'}$=3.9, H-2'-A); 4.34 (ddd, 1H, $J_{gem}$=11.5, $J_{H,P}$=7.4, $J_{5'b,4'}$=5.4, H-5'b-B); 4.39 (dd, 2H, $J_{H,P}$=7.6, $J_{5',4'}$=4.2, H-5'-A); 4.43 (ddd, 1H, $J_{gem}$=11.6, $J_{H,P}$=7.2, $J_{5'a,4'}$=2.9, H-5'a-B); 5.78 (d, 2H, $J_{5,6}$=8.0, H-5-A,B); 5.84 (d, 1H, $J_{1',2'}$=4.2, H-1'-B); 5.85 (d, 1H, $J_{1',2'}$=3.9, H-1'-A); 7.74 (d, 1H, $J_{6,5}$=8.0, H-6-A); 7.75 (d, 1H, $J_{6,5}$=8.0, H-6-B).

$^{13}$C NMR (125.7 MHz, CD$_3$OD): 14.45 (CH$_3$(CH$_2$)$_{12}$CH$_2$O-A,B); 21.33 (d, $J_{C,P}$=140.7, PCH$_2$CH$_2$N—B); 21.38 (d, $J_{C,P}$=141.1, PCH$_2$CH$_2$N-A); 23.28 (NCH$_2$CH$_2$CH$_2$NH$_2$-A,B); 23.73, 26.57, 30.32, 30.48, 30.68, 30.74, 30.76, 30.78, 30.79, 30.81 (CH$_3$(CH$_2$)$_{11}$CH$_2$CH$_2$O-A,B); 31.55 (d, $J_{C,P}$=5.8, CH$_3$(CH$_2$)$_{11}$CH$_2$CH$_2$O—B); 31.56 (d, $J_{C,P}$=5.9, CH$_3$(CH$_2$)$_{11}$CH$_2$CH$_2$O-A); 33.07 (CH$_3$(CH$_2$)$_{11}$CH$_2$CH$_2$O-A,B); 37.87 (NCH$_2$CH$_2$CH$_2$NH$_2$-A,B); 48.59 (NCH$_2$CH$_2$P-A,B); 51.09 (NCH$_2$CH$_2$CH$_2$NH$_2$-A,B); 67.36 (d, $J_{C,P}$=6.2, CH$_2$-5'-A); 67.37 (d, $J_{C,P}$=6.2, CH$_2$-5'-B); 68.37 (d, $J_{C,P}$=6.8, CH$_3$(CH$_2$)$_{12}$CH$_2$O—B); 68.56 (d, $J_{C,P}$=6.8, CH$_3$(CH$_2$)$_{12}$CH$_2$O-A); 70.81 (CH-3'-A); 70.90 (CH-3'-B); 74.61 (CH-2'-B); 74.66 (CH-2'-A); 83.37 (d, $J_{C,P}$=5,9, CH-4'-A); 83.39 (d, $J_{C,P}$=6.1, CH-4'-B); 92.12 (CH-1'-B); 92.24 (CH-1'-A); 103.17 (CH-5-B); 103.21 (CH-5-A); 142.99 (CH-6-B); 143.04 (CH-6-A); 152.23 (C-2-B); 152.28 (C-2-A); 165.96 (C-4-B); 165.97 (C-4-A).

$^{31}$P{$^1$H} NMR (202.3 MHz, CD$_3$OD): 27.66 (B); 28.12 (A).

IR $v_{max}$(CHCl$_3$) 3415 (s, vbr), 3045 (s, vbr, sh), 2924 (vs), 2854 (s), 2644 (m, vbr), 2563 (m, vbr), 2028 (w, vbr), 1972 (w, vbr, sh), 1690 (vs, br), 1624 (m), 1520 (w, br, sh), 1465 (m), 1407 (m), 1386 (m), 1266 (s), 1232 (s, sh), 1072 (s, sh), 1054 (s), 1015 (s, sh), 996 (s), 823 (m), 763 (w), 721 (w).

HR-ESI $C_{31}H_{61}O_8N_5P$ (M+H)$^+$ calculated 662.42523, found 662.42502.

Example 4

Tridecyl-uridine-5'-yl-2-N-bis (3-aminopropyl)-2-aminoethyl phosphonate

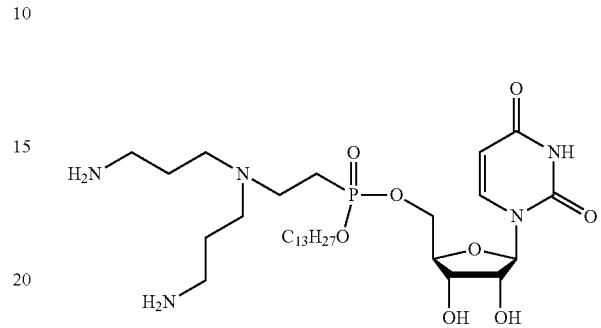

The compound in Example 4 was prepared by the same procedure as the one in Example 1 from boc-N-1-(3-aminopropyl)propane-1,3-diamine (0.95 g, 2.85 mmol) and tridecyl-2',3'-isopropylidenuridine-5'-yl-vinylphosphonate (prepared according to J. Med. Chem. 2011, 54(22), 7884-7898) (1.32 g, 2.38 mmol) in 65% yield (1.11 g, 1.54 mmol).

$^1$H NMR (500.0 MHz, CD$_3$OD): 0.90 (m, 6H, CH$_3$(CH$_2$)$_{11}$CH$_2$O); 1.24-1.43 (m, 40H, CH$_3$(CH$_2$)$_{10}$CH$_2$CH$_2$O); 1.68-1.75 (m, 4H, CH$_3$(CH$_2$)$_{10}$CH$_2$CH$_2$O); 2.18 (bm, 8H, NCH$_2$CH$_2$CH$_2$NH$_2$); 2.55 (m, 4H, PCH$_2$CH$_2$N); 3.09 (t, 8H, $J_{vic}$=7.4, NCH$_2$CH$_2$CH$_2$NH$_2$); 3.35 (m, 8H, NCH$_2$CH$_2$CH$_2$NH$_2$); 3.45 (m, 4H, PCH$_2$CH$_2$N); 4.09-4.20 (m, 8H, H-3',4', CH$_3$(CH$_2$)$_{11}$CH$_2$O); 4.26 (dd, 1H, $J_{2',3'}$=5.2, $J_{2',1'}$=4.0, H-2'); 4.28 (dd, 1H, $J_{2',3'}$=5.1, $J_{2',1'}$=3.9, H-2'); 4.33 (ddd, 1H, $J_{gem}$=11.4, $J_{H,P}$=7.6, $J_{5'b,4'}$=5.3, H-5'b); 4.38 (dd, 2H, $J_{H,P}$=7.6, $J_{5',4'}$=4.2, H-5'); 4.43 (ddd, 1H, J=11.4, $J_{H,P}$=7.4, $J_{5'a,4'}$=2.9, H-5'a); 5.759, 5.761 (2×d, 2×1H, $J_{5,6}$=8.1, H-5); 5.83 (d, 1H, $J_{1',2'}$=4.0, H-1'); 5.84 (d, 1H, $J_{1',2'}$=3.9, H-1'); 7.72, 7.73 (2×d, 2×1H, $J_{6,5}$=8.1, H-6).

$^{13}$C NMR (125.7 MHz, CD$_3$OD): 14.44 (CH$_3$(CH$_2$)$_{11}$CH$_2$O); 20.34 (d, $J_{C,P}$=141.8, PCH$_2$CH$_2$N); 23.40 (NCH$_2$CH$_2$CH$_2$NH$_2$); 23.74; 26.58; 30.32; 30.48; 30.68; 30.74; 30.77, 30.78, 30.80 (CH$_3$(CH$_2$)$_{10}$CH$_2$CH$_2$O); 31.57, 31.58 (d, $J_{C,P}$=6.0, CH$_3$(CH$_2$)$_{10}$CH$_2$CH$_2$O); 33.08 (CH$_3$(CH$_2$)$_9$CH$_2$CH$_2$N); 37.91 (NCH$_2$CH$_2$CH$_2$NH$_2$); 48.66 (PCH$_2$CH$_2$N); 51.17 (NCH$_2$CH$_2$CH$_2$NH$_2$); 67.41, 67.47 (d, $J_{C,P}$=6.3, CH$_2$-5'); 68.34, 68.55 (d, $J_{C,P}$=6.9, CH$_3$(CH$_2$)$_{10}$CH$_2$CH$_2$O); 70.87; 70.93 (CH-3'); 74.59; 74.63 (CH-2'); 83.35, 83.36 (d, $J_{C,P}$=6.2, CH-4'); 92.40, 92.47 (CH-1'); 103.13, 103.19 (CH-5); 143.03, 143.07 (CH-6); 152.20, 152.28 (C-2); 165.95, 165.96 (C-4).

$^{31}$P{$^1$H} NMR (202.3 MHz, CD$_3$OD): 27.57, 28.01.

IR $v_{max}$(KBr) 3424 (s, br), 3047 (br, sh), 2925 (vs), 2854 (s), 2642 (m, br), 2562 (w, br), 2030 (vw, vbr), 1975 (vw, vbr), 1690 (vs), 1465 (m), 1406 (m), 1385 (m), 1266 (m), 1232 (m, sh), 1075 (m), 1054 (m, br), 1035 (m, vbr), 996 (m), 821 (w), 764 (w), 721 (w). HR-ESI $C_{30}H_{59}O_8N_5P$ (M+H)$^+$ calculated 648.409583, found 648.409712.

Example 5

Dodecyl-uridine-5'-yl-2-N-bis(3-aminopropyl)-2-aminoethyl phosphonate

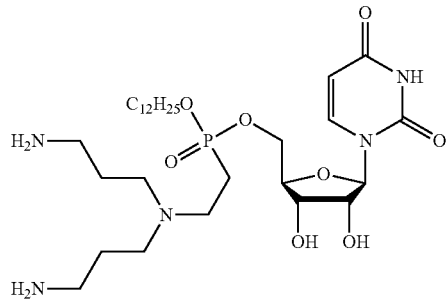

The compound in Example 5 was prepared by the same procedure as the one in Example 1 from boc-N-1-(3-aminopropyl)propane-1,3-diamine (0.53 g, 1.5 mmol) and dodecyl-2',3'-isopropylidenuridine-5'-yl-vinylphosphonate (prepared according to J. Med. Chem. 2011, 54(22), 7884-7898) (0.55 g, 1 mmol) in 41% yield (0.29 g, 0.41 mmol).

$^1$H NMR (600.1 MHz, CD$_3$OD): 0.90 (m, 6H, CH$_3$(CH$_2$)$_{10}$CH$_2$O); 1.25-1.42 (m, 36H, CH$_3$(CH$_2$)$_9$CH$_2$CH$_2$O); 1.71 (m, 4H, CH$_3$(CH$_2$)$_9$CH$_2$CH$_2$O); 2.22 (bm, 8H, NCH$_2$CH$_2$CH$_2$NH$_2$); 2.60 (m, 4H, PCH$_2$CH$_2$N); 3.11 (t, 8H, J$_{vic}$=7.4, NCH$_2$CH$_2$CH$_2$NH$_2$); 3.39 (m, 8H, NCH$_2$CH$_2$CH$_2$NH$_2$); 3.48 (m, 4H, PCH$_2$CH$_2$N); 4.08-4.22 (m, 8H, H-3',4', CH$_3$(CH$_2$)$_{10}$CH$_2$O); 4.27 (dd, 1H, J$_{2',3'}$=5.5, =4.2, H-2'); 4.29 (dd, 1H, J$_{2',3'}$=5.4, =4.0, H-2'); 4.34 (ddd, 1H, J$_{gem}$=11.4, J$_{H,P}$=7.5, J$_{5'b,4'}$=5.4, H-5'b); 4.39 (dd, 2H, J$_{H,P}$=7.5, J$_{5'4}$=4.3, H-5'); 4.44 (ddd, 1H, J=11.4, J$_{H,P}$=7.3, J$_{5'a,4'}$=2.9, H-5'a); 5.78 (d, 2H, J$_{5,6}$=8.1, H-5); 5.84 (d, 1H, J$_{1',2'}$=4.2, H-1'); 5.85 (d, 1H, J$_{1',2'}$=4.0, H-1'); 7.73, 7.74 (2×d, 2×1H, J$_{6,5}$=8.1, H-6).

$^{13}$C NMR (150.9 MHz, CD$_3$OD): 14.43 (CH$_3$(CH$_2$)$_{10}$CH$_2$O); 20.38, 21.42 (d, J$_{C,P}$=140.9, PCH$_2$CH$_2$N); 23.28 (NCH$_2$CH$_2$CH$_2$NH$_2$); 23.71; 26.56; 30.30; 30.46; 30.66; 30.72; 30.74, 30.76 (CH$_3$(CH$_2$)$_9$CH$_2$CH$_2$O); 31.55, 31.56 (d, J$_{C,P}$=5.9, CH$_3$(CH$_2$)$_9$CH$_2$CH$_2$O); 33.05 (CH$_3$(CH$_2$)$_9$CH$_2$CH$_2$N); 37.90 (NCH$_2$CH$_2$CH$_2$NH$_2$); 48.65 (PCH$_2$CH$_2$N); 51.13 (NCH$_2$CH$_2$CH$_2$NH$_2$); 67.35, 67.37 (d, J$_{C,P}$=6.2, CH$_2$-5'); 68.39, 68.57 (d, J$_{C,P}$=6.8, CH$_3$(CH$_2$)$_9$CH$_2$O); 70.83; 70.92 (CH-3'); 74.61; 74.66 (CH-2'); 83.40, 83.42 (d, J$_{C,P}$=6.1, CH-4') 92.13, 92.25 (CH-1'); 103.19, 103.23 (CH-5); 142.98, 143.02 (CH-6); 152.23, 152.28 (C-2); 165.93, 165.94 (C-4).

$^{31}$P{$^1$H} NMR (202.3 MHz, CD$_3$OD): 27.60, 28.05.

IR v$_{max}$(KBr) 3391 (s, br), 3000 (vs, vbr), 2925 (vs), 2854 (vs), 2645 (s, br), 2563 (m, br), 2031 (w, br), 1692 (vs, br), 1623 (m), 1575 (w, sh), 1515 (m, br, sh), 1465 (s), 1408 (m), 1385 (m), 1267 (s), 1233 (s, sh), 1077 (s, br, sh), 1058 (s, br, sh), 1036 (s, br), 998 (s, br), 823 (m), 763 (w), 721 (w).

HR-ESI C$_{29}$H$_{57}$O$_8$N$_5$P (M+H)$^+$ calculated 634.39393, found 634.39398.

Example 6

Pentadecyl-uridine-5'-yl-2-N-bis(3-aminoethyl)-2-aminoethyl phosphonate

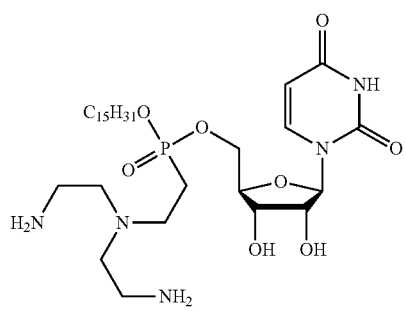

The compound in Example 6 was prepared by the same procedure as the one in Example 1 from boc-N-1-(2-aminoetyl)ethane-1,2-diamine (0.2 g, 0.66 mmol) (prepared according to J. Med. Chem. 2014, 57 (22), 9409-9423) and pentadecyl-2',3'-isopropylidenuridine-5'-yl-vinylphosphonate (prepared according to *J. Med. Chem.* 2011, 54(22), 7884-7898) (0.29 g, 0.5 mmol) in 50% yield (0.19 g, 0.25 mmol).

$^1$H NMR (500.0 MHz, CD$_3$OD): 0.90 (m, 6H, CH$_3$(CH$_2$)$_{13}$CH$_2$O); 1.23-1.44 (m, 48H, CH$_3$(CH$_2$)$_{12}$CH$_2$CH$_2$O); 1.70 (m, 4H, CH$_3$(CH$_2$)$_{12}$CH$_2$CH$_2$O); 2.16-2.29 (m, 4H, PCH$_2$CH$_2$N); 2.83-3.00 (m, 12H, NCH$_2$CH$_2$NH$_2$, PCH$_2$CH$_2$N); 3.09-3.17 (bm, 8H, NCH$_2$CH$_2$NH$_2$); 4.06-4.20 (m, 8H, H-3',4', CH$_3$(CH$_2$)$_{13}$CH$_2$O); 4.24-4.43 (m, 6H, H-2',5'); 5.755 (d, 1H, J$_{5,6}$=8.0, H-5); 5.757 (d, 1H, J$_{5,6}$=8.0, H-5); 5.808 (d, 1H, J$_{1',2'}$=3.7, H-1'); 5.812 (d, 1H, J$_{1',2'}$=3.9, H-1'); 7.71 (d, 1H, J$_{6,5}$=8.0, H-6); 7.72 (d, 1H, J$_{6,5}$=8.0, H-6).

$^{13}$C NMR (125.7 MHz, CD$_3$OD): 14.45 (CH$_3$(CH$_2$)$_{13}$CH$_2$O-A,B); 22.78 (d, J$_{C,P}$=138.3, PCH$_2$CH$_2$N); 22.84 (d, J$_{C,P}$=138.2, PCH$_2$CH$_2$N); 23.74, 26.64, 30.34, 30.48, 30.70, 30.75, 30.77, 30.79; 30.81 (CH$_3$(CH$_2$)$_{12}$CH$_2$CH$_2$O); 31.57 (d, J$_{C,P}$=6.0, CH$_3$(CH$_2$)$_{12}$CH$_2$CH$_2$O); 31.59 (d, J$_{C,P}$=6.0, CH$_3$(CH$_2$)$_{12}$CH$_2$CH$_2$O); 33.08 (CH$_3$(CH$_2$)$_{12}$CH$_2$CH$_2$O); 37.90, 37.95 (NCH$_2$CH$_2$NH$_2$); 47.34 (NCH$_2$CH$_2$P); 51.47, 51.53 (NCH$_2$CH$_2$NH$_2$); 66.78 (d, J$_{C,P}$=6.3, CH$_2$-5'); 66.95 (d, J$_{C,P}$=6.6, CH$_2$-5'); 67.89 (d, J$_{C,P}$=6.9, CH$_3$(CH$_2$)$_{13}$CH$_2$O); 67.93 (d, J$_{C,P}$=6.9, CH$_3$(CH$_2$)$_{13}$CH$_2$O); 70.81, 70.86 (CH-3'); 74.54, 74.63 (CH-2'); 83.34 (d, J$_{C,P}$=6.2, CH-4'); 83.39 (d, J$_{C,P}$=6.2, CH-4'); 92.66, 92.68 (CH-1'); 103.04, 103.05 (CH-5); 143.05, 143.09 (CH-6); 152.17, 152.20 (C-2); 165.99, 165.99 (C-4).

$^{31}$P{$^1$H} NMR (202.3 MHz, CD$_3$OD): 33.66.

v$_{max}$(KBr) 3423 (s, vbr), 3018 (s, vbr, sh), 2924 (vs), 2854 (vs), 2650 (m, vbr, sh), 2560 (m, vbr), 2032 (vw, vbr), 1946 (vw, vbr), 1691 (s, br), 1626 (m), 1466 (s), 1406 (m), 1387

(m), 1266 (m), 1237 (m, br, sh), 1074 (m, sh), 1052 (m, sh), 1021 (s, br), 1000 (m, br, sh), 822 (w), 767 (w), 722 (w).

HR-ESI $C_{30}H_{59}O_8N_5P$ (M+H)$^+$ calculated 648.40958, found 648.40969.

Example 7

Tetradecyl-uridine-5'-yl-2-N-bis(3-aminoethyl)-2-aminoethyl phosphonate

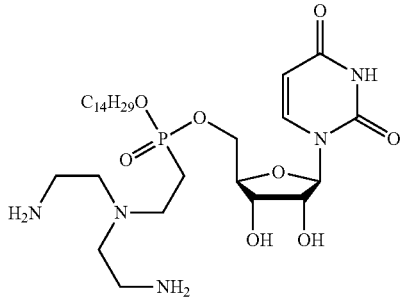

The compound in Example 7 was prepared by the same procedure as the one in Example 1 from boc-N-1-(2-aminoetyetyl)ethane-1,2-diamine (0.4 g, 1.32 mmol) and tetradecyl-2',3'-isopropylidenuridine-5'-yl-vinylphosphonate (0.63 g, 1.1 mmol) (prepared according to *J. Med. Chem.* 2011, 54(22), 7884-7898) in 37% yield (0.27 g, 0.41 mmol).

$^1$H NMR (500.0 MHz, CD$_3$OD): 0.90 (m, 6H, CH$_3$(CH$_2$)$_{12}$CH$_2$O-A,B); 1.13-1.46 (m, 44H, CH$_3$(CH$_2$)$_{11}$CH$_2$CH$_2$O-A,B); 1.71 (m, 4H, CH$_3$(CH$_2$)$_{11}$CH$_2$CH$_2$O-A,B); 2.28-2.49 (m, 4H, PCH$_2$CH$_2$N-A,B); 3.03-3.23 (m, 12H, NCH$_2$CH$_2$NH$_2$-A,B, PCH$_2$CH$_2$N-A,B); 3.23-3.33 (bm, 8H, NCH$_2$CH$_2$NH$_2$-A,B); 4.06-4.22 (m, 8H, H-3',4'-A,B, CH$_3$(CH$_2$)$_{13}$CH$_2$O-A,B); 4.24-4.44 (m, 6H, H-2',5'-A,B); 5.76 (d, 2H, $J_{5,6}$=8.0, H-5-A,B); 5.83 (d, 2H, $J_{1',2'}$=4.0, H-1'-A,B); 7.73 (d, 1H, $J_{6,5}$=8.0, H-6-B); 7.74 (d, 1H, $J_{6,5}$=8.0, H-6-A).

$^{13}$C NMR (125.7 MHz, CD$_3$OD): 14.45 (CH$_3$(CH$_2$)$_{12}$CH$_2$O-A,B); 22.35 (d, $J_{C,P}$=140.4, PCH$_2$CH$_2$N—B); 22.39 (d, $J_{C,P}$=141.7, PCH$_2$CH$_2$N-A); 23.74, 26.62, 30.34, 30.49, 30.69, 30.75, 30.77, 30.79, 30.80, 30.81 (CH$_3$(CH$_2$)$_{11}$CH$_2$CH$_2$O-A,B); 31.56 (d, $J_{C,P}$=6.0, CH$_3$(CH$_2$)$_{11}$CH$_2$CH$_2$O-A); 31.58 (d, $J_{C,P}$=6.0, CH$_3$(CH$_2$)$_{11}$CH$_2$CH$_2$O—B); 33.08 (CH$_3$(CH$_2$)$_{11}$CH$_2$CH$_2$O-A,B); 37.07 (NCH$_2$CH$_2$NH$_2$-A,B); 48.03 (NCH$_2$CH$_2$P); 51.48 (NCH$_2$CH$_2$NH$_2$—B); 51.51 (NCH$_2$CH$_2$NH$_2$-A); 66.95 (d, $J_{C,P}$=6.5, CH$_2$-5'-B); 67.05 (d, $J_{C,P}$=6.3, CH$_2$-5'-A); 68.08 (d, $J_{C,P}$=7.3, CH$_3$(CH$_2$)$_{12}$CH$_2$O)—B); 68.15 (d, $J_{C,P}$=7.4, CH$_3$(CH$_2$)$_{12}$CH$_2$O-A); 70.78 (CH-3'-B); 70.86 (CH-3'-A); 74.55 (CH-2'-A); 74.64 (CH-2'-B); 83.36 (d, $J_{C,P}$=6.0, CH-4'-B); 83.41 (d, $J_{C,P}$=6.2, CH-4'-A); 92.46 (CH-1'-A); 92.51 (CH-1'-B); 103.11 (CH-5-A,B); 143.07 (CH-6-B); 143.09 (CH-6-A); 152.21 (C-2-A); 152.25 (C-2-B); 165.95 (C-4-A); 165.98 (C-4-B).

$^{31}$P{$^1$H} NMR (202.3 MHz, CD$_3$OD): 31.69 (A,B).

IR $v_{max}$(KBr) 3427 (s, br), 3000 (s, vbr), 2956 (s), 2924 (vs), 2854 (s), 2560 (m, vbr), 2040 (vw, vbr), 1691 (s), 1466 (m), 1407 (w), 1387 (w), 1267 (m), 1235 (m, br, sh), 1073 (m, sh), 1051 (m, sh), 1018 (m), 1003 (m, sh), 824 (w), 766 (w, sh), 721 (vw).

HR-ESI $C_{29}H_{57}O_8N_5P$ (M+H)$^+$ calculated 634.39393, found 634.39391.

Example 8

Pentadecyl-uridine-5'-yl-2-N-bis(3-guanidinoethyl)-2-aminoethyl phosphonate

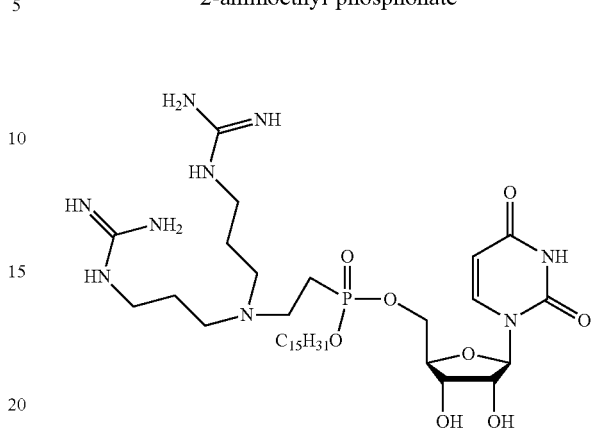

A mixture of 1H-pyrazol-1-carboxamidinuhydrochloride (0.24 g, 1.67 mol), the compound from Example 2 (0.5 g, 0.67 mmol) and dietylisopropylamine (0.57 mlL, 3.35 mmol) in DMF (10 ml) was stirred under argon at rt overnight. The solvent was evaporated and the product was obtained after reverse phase chromatography using a linear gradient of methanol in water (10-100%), evaporation and reprecipitation with ethyl acetate (50 ml) from a solution in 0.5 mol·l$^{-1}$ HCl in methanol (20 ml) in 64% yield (0.36 g, 0.43 mmol) as an amorphous solid.

$^1$H NMR (600.1 MHz, CD$_3$OD): 0.90 (m, 6H, CH$_3$(CH$_2$)$_{13}$CH$_2$O); 1.25-1.43 (m, 48H, CH$_3$(CH$_2$)$_{12}$CH$_2$CH$_2$O); 1.68-1.75 (m, 4H, CH$_3$(CH$_2$)$_{12}$CH$_2$CH$_2$O); 2.04-2.13 (bm, 8H, NCH$_2$CH$_2$CH$_2$NH); 2.48-2.60 (m, 4H, PCH$_2$CH$_2$N); 3.26-3.37 (m, 16H, NCH$_2$CH$_2$CH$_2$NH); 3.40-3.49 (m, 4H, PCH$_2$CH$_2$N); 4.10-4.20 (m, 8H, H-3',4', CH$_3$(CH$_2$)$_{12}$CH$_2$O); 4.25-4.29 (m, 2H, H-2'); 4.33 (ddd, 1H, $J_{gem}$=11.4, $J_{H,P}$=7.5, $J_{5'b,4'}$=5.3, H-5'b); 4.38 (dd, 2H, $J_{H,P}$=7.5, $J_{5',4'}$=4.2, H-5'); 4.43 (ddd, 1H, J=11.4, $J_{H,P}$=7.1, $J_{5'a,4'}$=2.9, H-5'a); 5.760, 5.763 (2×d, 2×1H, $J_{5,6}$=8.0, H-5); 5.83 (d, 1H, $J_{1',2'}$=4.2, H-1'); 5.84 (d, 1H, $J_{1',2'}$=3.9, H-1'); 7.724, 7.727 (2×d, 2×1H, $J_{6,5}$=8.0, H-6).

$^{13}$C NMR (150.9 MHz, CD$_3$OD): 14.43 (CH$_3$(CH$_2$)$_{13}$CH$_2$O); 21.36 (d, $J_{C,P}$=139.6, PCH$_2$CH$_2$N); 23.73 (NCH$_2$CH$_2$CH$_2$NH$_2$); 24.82, 26.59, 30.30, 30.31, 30.47, 30.68, 30.74, 30.76, 30.78, 30.79 (CH$_3$(CH$_2$)$_{12}$CH$_2$CH$_2$O); 31.56 (d, $J_{C,P}$=5.9, CH$_3$(CH$_2$)$_{12}$CH$_2$CH$_2$O); 33.07 (CH$_3$(CH$_2$)$_{12}$CH$_2$CH$_2$N); 39.70 (NCH$_2$CH$_2$CH$_2$NH); 48.40 (d, $J_{C,P}$=5.4, PCH$_2$CH$_2$N); 51.66 (NCH$_2$CH$_2$CH$_2$NH); 67.35 (d, $J_{C,P}$=6.4, CH$_2$-5'); 67.43 (d, $J_{C,P}$=6.3, CH$_2$-5'); 68.33 (d, $J_{C,P}$=6.9, CH$_3$(CH$_2$)$_{12}$CH$_2$CH$_2$O); 68.53 (d, $J_{C,P}$=6.7, CH$_3$(CH$_2$)$_{12}$CH$_2$CH$_2$O); 70.84, 70.88 (CH-3'); 74.62, 74.68 (CH-2'); 83.38, 83.43 (2×d, $J_{C,P}$=6.1, CH-4'); 92.37, 92.41 (CH-1'); 103.14, 103.19 (CH-5); 143.02, 143.03 (CH-6); 152.19, 152.25 (C-2); 158.69 (C-guanidine); 165.964, 165.970 (C-4).

$^{31}$P{$^1$H} NMR (202.3 MHz, CD$_3$OD): 27.79, 28.23.

IR $v_{max}$(KBr) 3424 (vs, vbr), 3260 (s, br, sh), 3183 (s, br), 2700 (w, vbr), 1694 (s, sh), 1671 (s), 1646 (s, sh), 1624 (s, sh), 1466 (m), 1387 (w), 1268 (m), 1223 (m, br), 1076 (w, sh), 1056 (m), 1036 (m, vbr), 1000 (m), 762 (w, br), 721 (w).

HR-ESI $C_{34}H_{67}O_8N_9P$ (M+H)$^+$ calculated 760.48447, found 760.48452.

Example 9

Tetradecyl-uridine-5'-yl-2-N-bis(3-guanidinoethyl)-2-aminoethyl phosphonate

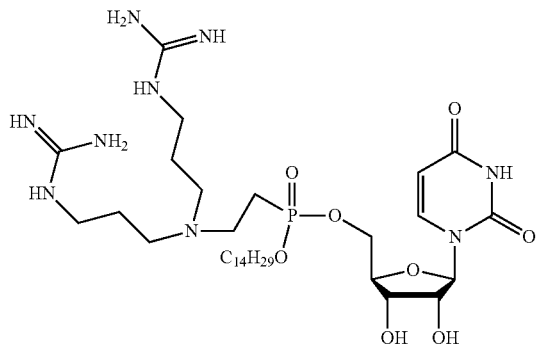

The compound in Example 9 was prepared by the same procedure as the compound in Example 8 from 1H-pyrazole-1-carboxamidinehydrochloride (1.8 g, 12.25 mmol), the compound from Example 3 (3 g, 4.1 mmol) and diethylisopropylamine (4, 2 ml, 24.6 mmol) in DMF (40 ml) in 59% yield (2.06 g, 2.41 mmol) as an amorphous solid.

$^1$H NMR (500.0 MHz, CD$_3$OD): 0.90 (m, 6H, CH$_3$(CH$_2$)$_{12}$CH$_2$O-A,B); 1.25-1.43 (m, 44H, CH$_3$(CH$_2$)$_{11}$CH$_2$CH$_2$O-A,B); 1.68-1.75 (m, 4H, CH$_3$(CH$_2$)$_{11}$CH$_2$CH$_2$O-A,B); 2.04-2.13 (bm, 8H, NCH$_2$CH$_2$CH$_2$NH-A,B); 2.52-2.64 (m, 4H, PCH$_2$CH$_2$N-A,B); 3.32-3.37 (m, 16H, NCH$_2$CH$_2$CH$_2$NH-A,B); 3.42-3.50 (m, 4H, PCH$_2$CH$_2$N-A,B); 4.11-4.20 (m, 8H, H-3',4'-A,B, CH$_3$(CH$_2$)$_{12}$CH$_2$O-A,B); 4.26 (dd, 1H, J$_{2',3'}$=5.3, J$_{2',1'}$=4.2, H-2'-B); 4.27 (dd, 1H, J$_{2',3'}$=5.2, J$_{2',1'}$=3.9, H-2'-A); 4.33 (ddd, 1H, J$_{gem}$=11.4, J$_{H,P}$=7.5, J$_{5b',4'}$=5.3, H-5'b-B); 4.38 (dd, 2H, J$_{H,P}$=7.5, J$_{5',4'}$=4.2, H-5'-A); 4.43 (ddd, 1H, J=11.4, J$_{H,P}$=7.1, J$_{5'a,4'}$=2.9, H-5'a-B); 5.77 (d, 2H, J$_{5,6}$=8.1, H-5-A,B); 5.84 (d, 1H, J$_{1',2'}$=4.2, H-1'-B); 5.85 (d, 1H, J$_{1',2'}$=3.9, H-1'-A); 7.747 (d, 1H, J$_{6,5}$=8.1, H-6-A); 7.752 (d, 1H, J$_{6,5}$=8.1, H-6-B).

$^{13}$C NMR (125.7 MHz, CD$_3$OD): 14.47 (CH$_3$(CH$_2$)$_{12}$CH$_2$O); 21.32 (d, J$_{C,P}$=141.3, PCH$_2$CH$_2$N-A,B); 23.76 (NCH$_2$CH$_2$CH$_2$NH$_2$-A,B); 24.76, 26.60, 30.33, 30.51, 30.71, 30.77, 30.79, 30.81, 30.83, 30.84 (CH$_3$(CH$_2$)$_{11}$CH$_2$CH$_2$O-A,B); 31.56 (d, J$_{C,P}$=6.1, CH$_3$(CH$_2$)$_{11}$CH$_2$CH$_2$O-A,B); 33.09 (CH$_3$(CH$_2$)$_{11}$CH$_2$CH$_2$N-A,B); 39.64 (NCH$_2$CH$_2$CH$_2$NH-A,B); 48.38 (PCH$_2$CH$_2$N-A,B); 51.56 (NCH$_2$CH$_2$CH$_2$NH-A,B); 67.31 (d, J$_{C,P}$=6.5, CH$_2$-5'-B); 67.37 (d, J$_{C,P}$=6.5, CH$_2$-5'-A); 68.31 (d, J$_{C,P}$=6.8, CH$_3$(CH$_2$)$_{11}$CH$_2$CH$_2$O-A); 68.51 (d, J$_{C,P}$=6.8, CH$_3$(CH$_2$)$_{11}$CH$_2$CH$_2$O—B); 70.78 (CH-3'-A); 70.84 (CH-3'-B); 74.63 (CH-2'-B); 74.70 (CH-2'-A); 83.37 (d, J$_{C,P}$=5.6, CH-4'-B); 83.42 (d, J$_{C,P}$=5.6, CH-4'-B); 92.13 (CH-1'-B); 92.20 (CH-1'-A); 103.13 (CH-5-B); 103.17 (CH-5-A); 143.00 (CH-6-B); 143.03 (CH-6-A); 152.19 (C-2-B); 152.24 (C-2-A); 158.62 (C-guanidine-A,B); 165.99 (C-4-B); 166.00 (C-4-A), $^{31}$P{$^1$H} NMR (202.3 MHz, CD$_3$OD): 27.83 (P-B); 28.28 (P-A).

IR v$_{max}$(KBr) 3320 (s, vbr), 3260 (s, vbr), 3155 (s, vbr), 2925 (s), 2854 (s), 2710 (m, vbr), 2604 (m), 2502 (m, vbr, sh), 1669 (vs, vbr), 1622 (vs, sh), 1465 (s), 1407 (m), 1379 (s), 1265 (s), 1235 (s, br, sh), 1075 (s, br, sh), 1045 (s), 1016 (s, br), 1002 (s, sh), 822 (m), 720 (w), 580 (m, vbr), 490 (m, br, sh).

HR-ESI C$_{33}$H$_{65}$O$_8$N$_9$P (M+H)$^+$ calculated 746.46882, found 746.46902.

Example 10

Tetradecyl-uridine-5'-yl-(3-aminopyrrolidin-1-N-yl)ethyl phosphonate

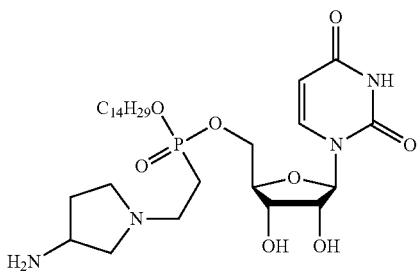

The compound in Example 10 was prepared by the same procedure as the one in Example 1 from 3-boc-3-aminopyrrolidine (0.51 g, 2.75 mmol) and tetradecyl-2',3'-isopropylidenuridine-5'-yl-vinylphosphonate (1.31 g, 2.3 mmol) (prepared according to *J. Med. Chem.* 2011, 54(22), 7884-7898) in 26% yield (0.384 g, 0.59 mmol).

$^1$H NMR (500.0 MHz, CD$_3$OD): 0.90 (m, 6H, CH$_3$(CH$_2$)$_{12}$CH$_2$O-A,B); 1.24-1.43 (m, 44H, CH$_3$(CH$_2$)$_{11}$CH$_2$CH$_2$O-A,B); 1.65-1.73 (m, 4H, CH$_3$(CH$_2$)$_{11}$CH$_2$CH$_2$O-A,B); 1.94-2.02 (bm, 2H, H-4b-pyrrolidine-A,B); 2.12-2.25 (bm, 6H, H-4b-pyrrolidine-A,B, PCH$_2$CH$_2$N-A,B); 2.89-3.02 (bm, 4H, PCH$_2$CH$_2$N-A,B); 3.24 (bdd, 2H, J$_{gem}$=12.2, J$_{2b,3}$=3.5, H-2b-pyrrolidine-A,B); 3.29-3.36 (m, 4H, H-2a, 5b-pyrrolidine-A,B); 3.43-3.49 (m, 2H, H-5a-pyrrolidine-A,B); 3.62 (bm, 2H, H-3-pyrrolidine-A,B); 4.04-4.17 (m, 8H, H-3',4'-A,B, CH$_3$(CH$_2$)$_{12}$CH$_2$O-A,B); 4.21-4.39 (m, 6H, H-2',5'-A,B); 5.73 (d, 2H, J$_{5,6}$=8.0, H-5-A,B); 5.83 (d, 2H, J$_{1',2'}$=3.9, H-1'-A,B); 7.71 (d, 1H, J$_{6,5}$=8.0, H-6-B); 7.72 (d, 1H, J$_{6,5}$=8.0, H-6-A).

$^{13}$C NMR (125.7 MHz, CD$_3$OD): 14.44 (CH$_3$(CH$_2$)$_{12}$CH$_2$O-A,B); 23.74 (CH$_3$(CH$_2$)$_{11}$CH$_2$CH$_2$O-A,B); 26.08 (d, J$_{C,P}$=139.9, PCH$_2$CH$_2$N-A,B); 26.65, 26.66, 30.29, 30.30, 30.48, 30.67, 30.68, 30.72, 30.73, 30.77, 30.78, 30.79, 30.81 (CH$_3$(CH$_2$)$_{11}$CH$_2$CH$_2$O-A,B); 31.03 (CH$_2$-4-pyrrolidine-A,B); 31.57 (b, J$_{C,P}$=6.1, CH$_3$(CH$_2$)$_{11}$CH$_2$CH$_2$O-A); 31.58 (d, J$_{C,P}$=6.1, CH$_3$(CH$_2$)$_{11}$CH$_2$CH$_2$O—B); 33.08 (CH$_3$(CH$_2$)$_{11}$CH$_2$CH$_2$O-A,B); 42.13 (d, J$_{C,P}$=2.5, NCH$_2$CH$_2$P-A,B); 45.29 (CH$_2$-5-pyrrolidine-A,B); 50.72, 50.79 (CH$_2$-2-pyrrolidine-A,B); 57.60 (CH-3-pyrrolidine-B); 57.63 (CH-3-pyrrolidine-A); 66.55 (d, J$_{C,P}$=6.6, CH$_2$-5'-A); 66.63 (d, J$_{C,P}$=6.5, CH$_2$-5'-B); 67.68 (d, J$_{C,P}$=6.9, CH$_3$(CH$_2$)$_{12}$CH$_2$O—B); 67.78 (d, J$_{C,P}$=6.9, CH$_3$(CH$_2$)$_{12}$CH$_2$O-A); 70.84 (CH-3'-A,B); 74.83 (CH-2'-A); 74.86 (CH-2'-B); 83.48 (d, J$_{C,P}$=6.4, CH-4'-A); 83.51 (d, J$_{C,P}$=6.3, CH-4'-B); 92.16 (CH-1'-A); 92.24 (CH-1'-B); 102.97 (CH-5-A,B); 142.75 (CH-6-A); 142.78 (CH-6-B); 152.16 (C-2-A); 152.17 (C-2-B); 165.98 (C-4-A); 165.99 (C-4-B).

$^{31}$P{$^1$H} NMR (202.3 MHz, CD$_3$OD): 32.16 (A); 32.36 (B).

IR v$_{max}$(CHCl$_3$) 3415 (s, vbr), 3051 (s, br), 2924 (vs), 2854 (vs), 2755 (m, vbr, sh), 2455 (w, vbr), 2030 (vw, vbr), 1970 (vw, vbr), 1693 (vs, br), 1464 (s), 1405 (m, sh), 1385 (m), 1261 (s, br), 1224 (m), 1075 (s, sh), 1053 (s), 1036 (s, sh), 1019 (s, sh), 996 (s), 822 (m), 766 (w), 721 (w).

HR-ESI $C_{29}H_{54}O_8N_4P$ (M+H)$^+$ calculated 617.36738, found 617.36742.

Antibacterial Activity

Antibacterial activity was measured using a standard microdilution method, showing the minimum inhibitory concentration (MIC) of the test sample which results in inhibition of bacterial growth. Disposable microtiter plates were used for the tests. Samples are dissolved in the brain-heart infusion broth (HiMedia Laboraties Pvt. Ltd., Czech Republic), and Mueller Hinton broth (HiMedia Laboraties, see above) at a final concentration ranging from 200 µg/ml to 1.5625 µg/ml. Plates were inoculated with a standard amount of test bacteria—inoculum density in the hole corresponds to $10^{5-6}$ CFU/ml (colony forming units/ml). MIC values are read after 24/48 hours of incubation at 37° C. as the minimum inhibitory concentration of the test substance at which the growth of bacteria is inhibited. Minimal bactericidal concentration (MBC) is defined as the minimum concentration of the sample needed to achieve irreversible inhibition, therefore killing the bacteria after a defined time of incubation. The MBC was determined by inoculation method. 10 µl from the wells in a microplate with a defined concentration of test substance is taken with an applicator, and inoculated onto the surface of blood agar (Trios, Czech Republic) and Sabouraud agar (Trios, CR). The MBC was determined as the lowest concentration that inhibited visible growth of the bacteria used.

Standard reference bacterial strains (*Escherichia coli* CCM 3954, *Pseudomonas aeruginosa* CCM 3955, *Enterococcus faecalis* CCM 4224, *Staphylococcus aureus* CCM 4223) were obtained from the Czech Collection of Microorganisms (CCM) at Masaryk University in Brno. *Streptococcus agalactiae*, *Bacillus subtilis* were obtained from the University Hospital Olomouc. The tested microorganisms were maintained in cryobanks (ITEST plus, Czech Republic) at −80° C.

TABLE 1

Minimum inhibitory concentrations of lipophosphonoxins of the present invention against a panel of reference bacterial strains

| | MIC µg/ml | | | | | |
|---|---|---|---|---|---|---|
| Compound from example | *Escherichia coli* CCM 3954 | *Pseudomonas aeruginosa* CCM 3955 | *Enterococcus faecalis* CCM 4224 | *Staphylococcus aureus* CCM 4223 | *Bacillus subtilis* | *Streptococcus agalactiae* |
| 1 | 3.125 | 6.25 | 50 | 12.5 | 0.78 | 3.125 |
| 2 | 6.25 | 3.125 | 50 | 6.25 | 1.56 | 3.125 |
| 3 | 6.25 | 0.78 | 25 | 6.25 | 0.78 | 3.125 |
| 4 | 25 | 3.125 | 50 | 12.5 | 3.125 | 6.25 |
| 5 | 25 | 3.125 | 100 | 25 | 3.125 | 12.5 |
| 6 | 1.56 | 1.56 | 12.5 | 6.25 | 0.78 | 3.125 |
| 7 | 12.5 | 3.125 | 100 | 25 | 6.25 | 6.25 |
| 8 | 0.78 | 0.78 | 25 | 3.125 | 0.39 | 1.56 |
| 9 | 3.125 | 3.125 | 12.5 | 6.25 | 1.56 | 3.125 |
| 10 | 3.125 | 3.125 | 6.25 | 12.5 | 1.56 | 3.125 |

TABLE 2

Minimum inhibitory concentrations of lipophosphonoxins of the present invention against a panel of reference bacterial strains

| | MIC µg/ml | | | |
|---|---|---|---|---|
| Compound from example | *Salmonella Enteritidis* S2-25 | *Acinetobacter baumanii* A3-08 | *Stenotrophomonas matophilia* S2-23 | *Burkholderia multivorans* ATCC BAA-247 |
| 2 | 3.125 | 6.25 | 3.125 | 12.5 |
| 3 | 6.25 | 25 | 50 | 200 |
| 4 | 50 | 50 | 50 | 50 |
| 7 | 12.5 | 25 | 6.25 | 12.5 |
| 8 | 1.56 | 6.25 | 3.125 | 100 |
| 9 | 3.125 | 12.5 | 12.5 | 100 |

TABLE 3

Minimum inhibitory concentrations of some of lipophosphonoxins of the present invention against a panel of resistant bacterial strains

| | MIC µg/ml | | | | | |
|---|---|---|---|---|---|---|
| Compound from example | *E. coli* 16702 | *P. aeruginosa* 16575 | *S. aureus* MRSA 4591 | *S. haemolyticus* 16568 | *E. faecium* VanA 419ana | *S. epidermidis* 8700B |
| 1 | 3.125 | 3.125 | 25 | 3.125 | 25 | 3.125 |
| 2 | 6.25 | 3.125 | 12.5 | 3.125 | 25 | 6.25 |
| 3 | 3.125 | 1.56 | 6.25 | 1.56 | 100 | 1.56 |
| 4 | 50 | 25 | 25 | 6.25 | 100 | 12.5 |

TABLE 3-continued

Minimum inhibitory concentrations of some of lipophosphonoxins of the present invention against a panel of resistant bacterial strains

| Compound from example | E. coli 16702 | P. aeruginosa 16575 | S. aureus MRSA 4591 | S. haemolyticus 16568 | E. faecium VanA 419ana | S. epidermidis 8700B |
|---|---|---|---|---|---|---|
| 5 | 25 | 12.5 | 50 | 12.5 | 200 | 12.5 |
| 6 | 1.56 | 1.56 | 6.25 | 1.56 | 100 | 1.56 |
| 7 | 6.25 | 6.25 | 12.5 | 3.125 | 100 | 3.125 |
| 8 | 0.78 | 1.56 | 3.125 | 1.56 | 50 | 1.56 |
| 9 | 3.125 | 6.25 | 6.25 | 3.125 | 50 | 3.125 |
| 10 | 3.125 | 3.125 | 25 | 6.25 | 50 | 3.125 |

*Multidrug-resistant bacterial strains isolated from clinical specimens from patients in University Hospital Olomouc: MRSA—methicillin-resistant *Staphylococcus aureus* 4591, *Staphylococcus haemolyticus* (a fluoroquinolone-resistant strain) 16568, *Enterococcus faecium* (vancomycin-resistant strain) VanA 419/ana, *Staphylococcus epidermidis* (methicillin-resistant strain) 8700/B In all cases, the value of the minimum inhibitory concentration (MIC) which is the concentration of test substance in the medium, which inhibited 100% of the growth of the tested bacteria, was equal to the minimum bactericidal concentration (MBC) which is the concentration at which 100% of the tested bacteria were killed. The MBC value was tested so that the bacteria tested for MIC were inoculated into a medium, which did not contain an inhibitor, and were monitored for growth.

Benefits of Lipophosphonoxins of the Second Generation:

Compared to LPPO of the first generation (*J. Med. Chem.* 2011, 54(22), 7884-7898, CZ PV 2011-312, EP2527351), the LPPO of the second generation show a much broader spectrum of antibacterial activity. Surprisingly, they are mainly effective against clinically important gram-negative bacterial strains and against harmful multiresistant bacterial strains occurring in the hospital environment.

According to the OECD404 test for skin irritation in rabbits, LPPO, specifically the compound of Example 3, is not an irritant.

Maximum tolerated dose in mice was very high, for the compound of Example 3 and oral administration the maximum tolerated dose was 1500 mg/kg of bodyweight.

The mechanism of action of LPPO of the second generation consists in the selective disruption of the bacterial cell membrane.

LPPO are well soluble in water.

LPPO exhibit high stability at a wide pH range (1-8).

Resistance formation against LPPO is very unlikely, since LPPO directly target the cell membrane, which is crucial for the life of the bacteria.

INDUSTRIAL APPLICABILITY

As antibacterial agents, lipophosphonoxins of this invention can be used as active ingredients of pharmaceutical compositions for the treatment of even very resistant bacterial infections, as ingredients of disinfectants and/or of selective culture media.

The invention claimed is:

1. Lipophosphonoxins of general formula I,

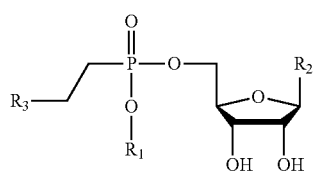

wherein
$R_1$ is selected from C8-C22 alkyl, hexadecyloxypropyl, tetradecyloxypropyl, tetradecyloxyethyl, hexadecyloxyetyl hexadecyloxyethyl;
$R_2$ is selected from uracil, thymine, cytosine; and
$R_3$ is selected from the group consisting of compounds of formulas II-V:

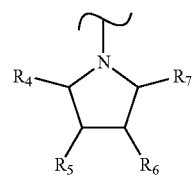

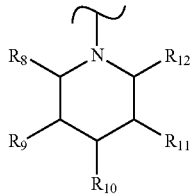

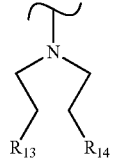

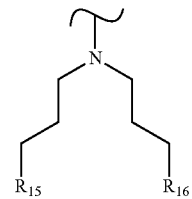

wherein $R_4$ is H, $CH_2NH_2$ or $CH_2OH$,
$R_5$ is H, $NH_2$ or OH,
$R_6$ is H, $NH_2$ or OH,
$R_7$ is H, $CH_2NH_2$ or $CH_2OH$,
$R_8$ is H, $CH_2NH_2$ or $CH_2OH$,
$R_9$ is H, $NH_2$ or OH,
$R_{10}$ is H, $NH_2$ or OH,
$R_{11}$ is H, $NH_2$ or OH, $R_{12}$ is H, $CH_2NH_2$ or $CH_2OH$,
$R_{13}$ is $NH_2$ or —NH—$C(NH_2)NH$,
$R_{14}$ is $NH_2$ or —NH—$C(NH_2)NH$,
$R_{15}$ is $NH_2$ or NH—$CH(NH_2)NH$,
$R_{16}$ is $NH_2$ or NH—$CH(NH_2)NH$, whereas at least one of $R_5$ and $R_6$ groups must be $NH_2$ or at least one of $R_4$ and $R_7$ groups must be $CH_2NH_2$, and whereas at least one of $R_9$, $R_{11}$ and $R_{10}$ groups must be $NH_2$ or at least one of $R_8$ and $R_{12}$ groups must be $CH_2NH_2$;

and their pharmaceutically acceptable salts and/or hydrates.

2. Lipophosphonoxins of general formula I according to claim 1, or pharmaceutically acceptable salts and/or hydrates and/or mixtures of such compounds, for use as a medicament.

3. Lipophosphonoxins of general formula I according to claim 1 or their diastereomers, or pharmaceutically acceptable salts and/or hydrates and/or mixtures of such compounds, for use as an antibacterial agent.

4. Antibacterial drug, characterized in that it contains at least one lipophosphonoxin of general formula I according to claim 1, or a diastereomer, or a pharmaceutically acceptable salt and/or hydrate, and/or a mixture of such compounds as the active ingredient.

5. Disinfectant for other than therapeutic purposes and/or selective culture medium characterized in that it contains at least one lipophosphonoxin of general formula I according to claim 1, or its diastereomer, or a pharmaceutically acceptable salt and/or hydrate, and/or mixture of such compounds as the active ingredient.

6. A method of treatment of bacterial infections comprising the step of administering the lipophosphonoxins of Formula I according to claim 1, or their diastereomers, or pharmaceutically acceptable salts and hydrates, and/or mixtures of such compounds to the subject in need of such treatment.

7. A method of preparation of a disinfectant comprising the step of providing lipophosphonoxins of Formula I according to claim 1, or their diastereomers, or pharmaceutically acceptable salts and/or hydrates, and/or mixtures of such compounds.

8. A method of preparation of selective cultivation medium for in vitro cultures comprising the step of providing lipophosphonoxins of Formula I according to claim 1, or their diastereomers, or pharmaceutically acceptable salts and/or hydrates, and/or mixtures of such compounds.

* * * * *